US011890625B2

(12) United States Patent
Adam

(10) Patent No.: US 11,890,625 B2
(45) Date of Patent: *Feb. 6, 2024

(54) DEVICE FOR DISPENSING A FLUID PRODUCT, AND METHOD FOR FILLING AND FOR PLUGGING SAME

(71) Applicant: APTAR FRANCE SAS, Le Neubourg (FR)

(72) Inventor: Fabien Adam, Aviron (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/967,050

(22) Filed: Oct. 17, 2022

(65) Prior Publication Data

US 2023/0110149 A1 Apr. 13, 2023

Related U.S. Application Data

(63) Continuation of application No. 17/257,093, filed as application No. PCT/FR2019/051741 on Jul. 11, 2019, now Pat. No. 11,478,809.

(30) Foreign Application Priority Data

Jul. 12, 2018 (FR) ...................................... 1856405

(51) Int. Cl.
| | | |
|---|---|---|
| *B05B 11/00* | (2023.01) | |
| *B05B 11/02* | (2023.01) | |
| *B65B 3/00* | (2006.01) | |
| *B65B 31/02* | (2006.01) | |

(Continued)

(52) U.S. Cl.
CPC ....... *B05B 11/0097* (2013.01); *A61M 11/007* (2014.02); *A61M 15/0036* (2014.02);
(Continued)

(58) Field of Classification Search
CPC ................. B05B 11/0097; B05B 11/02; B05B 11/00416; B05B 11/028; B65B 3/003;
(Continued)

(56) References Cited

U.S. PATENT DOCUMENTS

| | | |
|---|---|---|
| 5,813,570 A | 9/1998 | Fuchs et al. |
| 6,626,379 B1 | 9/2003 | Ritsche et al. |

(Continued)

FOREIGN PATENT DOCUMENTS

| | | |
|---|---|---|
| FR | 2668119 A2 | 4/1992 |
| FR | 2692569 A1 | 12/1993 |

(Continued)

OTHER PUBLICATIONS

International search report for PCT/FR2019/051741 dated Jan. 7, 2020.

(Continued)

*Primary Examiner* — Frederick C Nicolas
(74) *Attorney, Agent, or Firm* — Sughrue Mion, PLLC

(57) ABSTRACT

A fluid dispenser device including a body; a reservoir containing one or two doses of a fluid, the reservoir including a stopper that closes the reservoir in leaktight manner before actuation; a dispenser head that is provided with a dispenser orifice; and dispenser mechanism for dispensing at least a portion of the fluid through the dispenser orifice during actuation. The device further includes a needle having a tip that is adapted to pierce the stopper during actuation, the reservoir being filled with the fluid and being closed with the stopper under a vacuum, so that the residual volume of air present in the reservoir between the fluid and the stopper is substantially zero.

6 Claims, 2 Drawing Sheets

(51) Int. Cl.
*B65B 7/28* (2006.01)
*A61M 11/00* (2006.01)
*A61M 15/00* (2006.01)

(52) U.S. Cl.
CPC ............ *B05B 11/02* (2013.01); *B05B 11/028* (2023.01); *B65B 3/003* (2013.01); *B65B 7/2821* (2013.01); *B65B 31/027* (2013.01); *A61M 15/0021* (2014.02); *A61M 2210/0618* (2013.01)

(58) Field of Classification Search
CPC ................ B65B 7/2821; B65B 31/027; A61M 15/0021; A61M 2210/0618; A61M 11/007; A61M 15/0036
See application file for complete search history.

(56) References Cited

U.S. PATENT DOCUMENTS

| | | | |
|---|---|---|---|
| 6,708,846 B1 | 3/2004 | Fuchs et al. | |
| 7,299,949 B2 | 11/2007 | Greiner-Perth | |
| 11,478,809 B2 * | 10/2022 | Adam | ................. B05B 11/0097 |
| 2005/0023295 A1 | 2/2005 | Tempfli | |
| 2005/0029288 A1 | 2/2005 | Heldt et al. | |
| 2015/0284115 A1 | 10/2015 | Voth et al. | |
| 2017/0296758 A1 | 10/2017 | Petit | |
| 2020/0254465 A1 | 8/2020 | Brouet | |

FOREIGN PATENT DOCUMENTS

| | | |
|---|---|---|
| FR | 2706137 A1 | 12/1994 |
| WO | 2010001049 A2 | 1/2010 |

OTHER PUBLICATIONS

International Preliminary Report on Patentability with English Translation of Written Opinion dated Jan. 12, 2021 from the International Bureau in International Application No. PCT/FR2019/051741.

* cited by examiner

DEVICE FOR DISPENSING A FLUID PRODUCT, AND METHOD FOR FILLING AND FOR PLUGGING SAME

CROSS-REFERENCE TO RELATED APPLICATIONS

This application is a continuation of U.S. application Ser. No. 17/257,093, filed on Dec. 30, 2020, which is a National Stage of International Application No. PCT/FR2019/051741 filed Jul. 11, 2019, which claims priority under U.S.C. § 119(a) to French Patent Application No. 1856405 filed on Jul. 12, 2018.

FIELD OF INVENTION

The present invention relates to a fluid dispenser device and to a method of filling and closing said device.

BACKGROUND

More particularly, the present invention relates to a fluid dispenser device including a fluid dispenser head for dispensing one or two doses of a pharmaceutical fluid. In that type of device, generally referred to as a single-dose or two-dose device, each dose of fluid, which is generally a liquid, is dispensed or sprayed through a dispenser orifice while the device is being actuated manually. If the device is a single-dose device, all of the fluid is dispensed in a single actuation. If the device is a two-dose device, the fluid is dispensed in two successive actuations of the device.

Generally, that type of single-dose or two-dose device is used for dispensing fluid nasally, orally, or sublingually. For nasal dispensing, the dispenser head then includes an axial extension that is adapted to penetrate into a user's nostril during use.

That type of device may present certain drawbacks. Thus, the reservoir generally contains an air bubble that is associated with filling and closing the reservoir, with a risk of the fluid contained in the reservoir being contaminated as a result. Furthermore, the presence of the air bubble may generate variations in the spray between different devices, which is generally not desirable. It is also possible for there to be a risk of the device blocking hydraulically, as a result of the compressibility of said air bubble. Said air bubble also limits the ability to compensate for manufacturing tolerances of the device.

Documents FR 2 692 569, WO 2010/001049, FR 2 668 119, and FR 2 706 137 form part of the prior art.

CERTAIN OBJECTS OF INVENTION

An object of the present invention is to provide a fluid dispenser device that does not have the above-mentioned drawbacks.

More particularly, an object of the present invention is to provide a device that limits the risk of contaminating the fluid before dispensing.

Another object of the present invention is to provide such a device that improves the reproducibility of the spray.

Another object of the present invention is to provide such a device that limits the risk of blocking the device during actuation.

Another object of the present invention is to provide such a device that makes it possible to compensate for manufacturing tolerances better.

Another object of the present invention is to provide such a device that is simple and inexpensive to manufacture and to assemble.

The present invention thus provides a fluid dispenser device comprising: a body; a reservoir containing one or two doses of a fluid, said reservoir including a stopper that closes said reservoir in leaktight manner before actuation; a dispenser head that is provided with a dispenser orifice; and dispenser means for dispensing at least a portion of said fluid through said dispenser orifice during actuation; said device including a needle having a tip that is adapted to pierce said stopper during actuation, said reservoir being filled with said fluid and being closed with said stopper under a vacuum, so that the residual volume of air present in said reservoir between said fluid and said stopper is substantially zero.

Advantageously, said stopper is in contact with said fluid in the reservoir.

Advantageously, said needle is stationary relative to said dispenser orifice.

The present invention also provides a method of filling and closing a fluid dispenser device comprising: a body; a reservoir containing one or two doses of a fluid, said reservoir including a stopper that closes said reservoir in leaktight manner before actuation; a dispenser head that is provided with a dispenser orifice; and dispenser means for dispensing at least a portion of said fluid through said dispenser orifice during actuation; said device including a needle having a tip that is adapted to pierce said stopper during actuation, said method comprising the following steps:

filling an empty reservoir in a filler unit;
arranging said filled reservoir in a closure unit that is provided with a vacuum chamber;
creating a vacuum in said vacuum chamber; and
closing said reservoir under a vacuum with said stopper.

Advantageously, said closure unit comprises: a support device; a vacuum chamber; a funnel; and a closure tool.

Advantageously, said step of filling an empty reservoir in a filler unit is also performed under a vacuum.

BRIEF DESCRIPTION OF FIGURES

These and other characteristics and advantages of the present invention appear more clearly from the following detailed description, given by way of non-limiting examples, and with reference to the accompanying drawings, and in which.

DETAILED DESCRIPTION OF NON-LIMITING EMBODIMENTS

The terms "proximal" and "distal" are relative to the dispenser orifice. The terms "axial" and "radial" are relative to the longitudinal central axis of the device.

Figure 1:
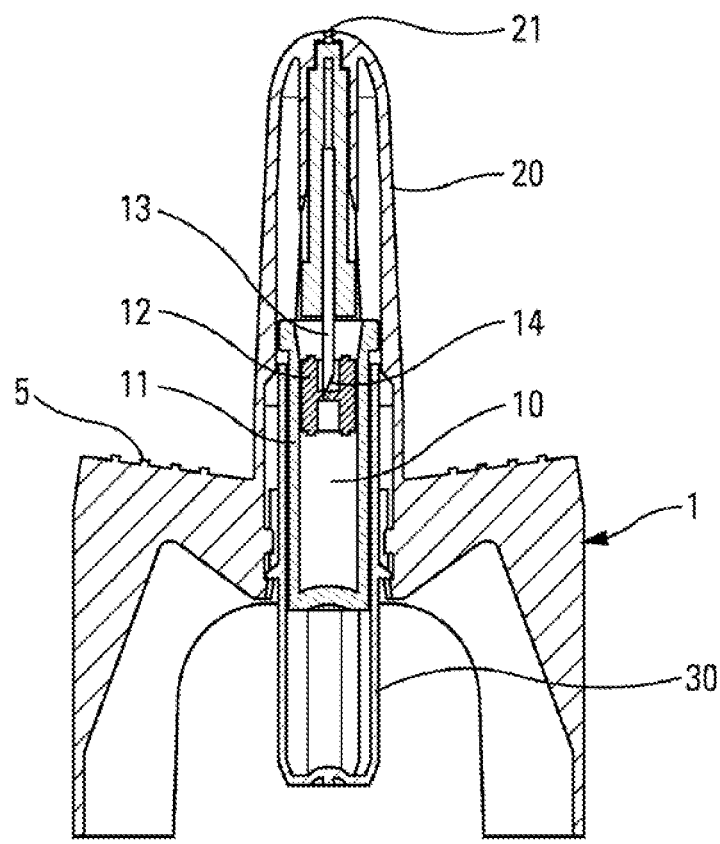
FIG. 1 is a diagrammatic section view of a nasal fluid dispenser device in an advantageous embodiment.

FIG. 1 shows an example of a nasal fluid dispenser device to which the present invention applies. In this example, the device is a single-dose device in which all of the dose of fluid is dispensed in a single actuation. It should be observed that the present invention could also be adapted to other types of device, e.g. such as devices of the two-dose type, containing two doses of fluid to be dispensed in two successive actuations of the device.

The device includes a body 1 including a radial flange 5 on which the user's fingers bear during actuation.

A dispenser head 20, in this example of the nasal type, extends axially from said radial flange 5 and includes a dispenser orifice 21 that is oriented axially. The dispenser orifice 21 serves to dispense a dose of fluid out from said dispenser head 20 while the device is being actuated by a user, such dispensing being performed by dispenser means. Advantageously, the nasal dispenser head 20 is made integrally with said body 1. It should be observed that the present invention could also apply to a device including an oral dispenser head. More generally, the present invention applies to all types of single-dose or two-dose devices.

The body 1 receives a reservoir 10. Typically, the reservoir 10 may be formed by a body 11 that is hollow and blind, including a single opening that is closed by a stopper 12 and containing a single dose of fluid to be dispensed during a single actuation of the device. Naturally, in the context of a two-dose device, the reservoir could contain two doses of fluid to be dispensed in two successive actuations.

The dispenser head 20 includes passage means that, during actuation, connect the reservoir 10 to the dispenser orifice 21. The passage means include a hollow needle 13 that includes a tip 14 that is adapted to pierce the stopper 12 at the time of actuation. Preferably, the needle 13 is stationary relative to the body 1, and in particular relative to the dispenser orifice 21.

Actuator means 30 may be provided so as to make it possible to actuate the device. Specifically, the actuator means 30 comprise an actuator body that is movable relative to the body 1, said actuator body co-operating with said reservoir 10 so as to move it axially relative to the body 1 and thus relative to the needle 13, towards the dispenser orifice 21. During this movement, the tip 14 of the needle 13 pierces the stopper 12, then said stopper slides in the reservoir 10 so as to expel the fluid through said needle 13. In this embodiment, the stopper 12 forms the dispenser means. In a variant, the actuator means could be formed by the bottom of the reservoir itself.

In another embodiment that is not shown in the drawings, the reservoir need not be formed by a hollow and blind body that includes only one opening, but may be formed by a hollow cylinder that is open axially at both ends. The cylinder would thus be closed at the proximal end by a first stopper and at the distal end by a second stopper, the volume defined between said two stoppers containing the fluid to be dispensed. When the user actuates the device, the user presses axially on the actuator body so as to slide it axially towards the dispenser orifice, as described above. This causes the second stopper to move inside the reservoir. However, since the fluid is incompressible, the movement of the second stopper thus moves the first stopper towards the needle, which is stationary. The first stopper is thus pierced by the needle and the contents of the reservoir are dispensed through said needle by the second stopper which thus acts as a piston. In this embodiment, the second stopper forms the dispenser means.

As described above, the invention could also apply to a device of the two-dose type. In this configuration, the contents of the reservoir would be dispensed in two successive actuations. Document WO 2014/147329 describes an example of a two-dose device.

In the invention, the reservoir 10 is filled with said fluid and then closed with said stopper 12, and at least this closure operation is performed under a vacuum in a closure unit that is provided with a vacuum chamber.

Figure 2:
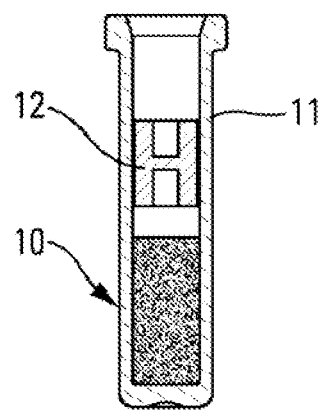
FIG. 2 is a diagrammatic view of a reservoir adapted to the FIG. 1 device, and filled at atmospheric pressure.
Figure 3:
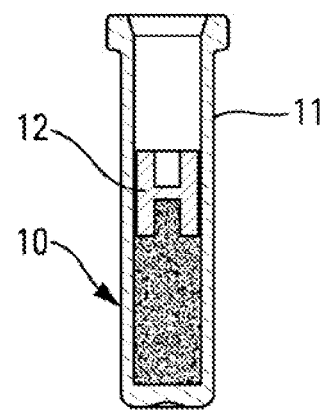
FIG. 3 is a view similar to the view in FIG. 2, with the reservoir filled under a vacuum.
Figure 4:
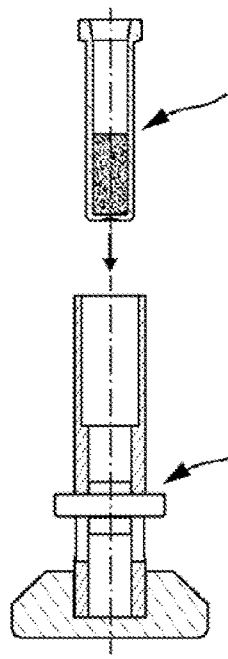
FIGS. 4 to 8 are diagrammatic views showing the stages of filling and closing the FIG. 3 reservoir.
Figure 5:
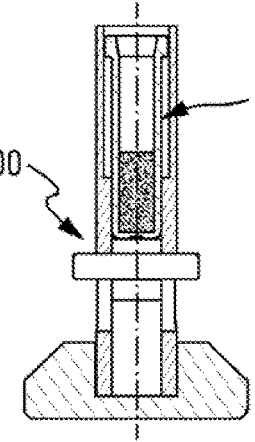
Figure 6:
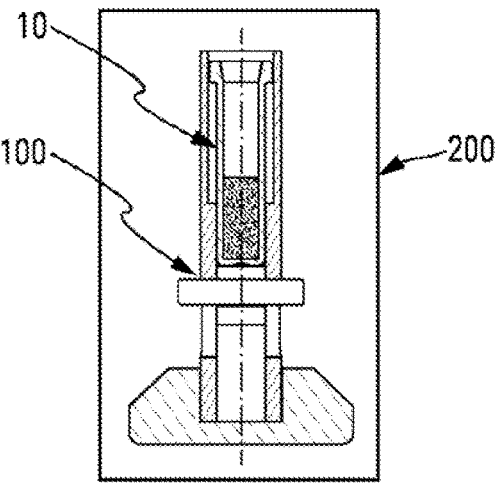
Figure 7:
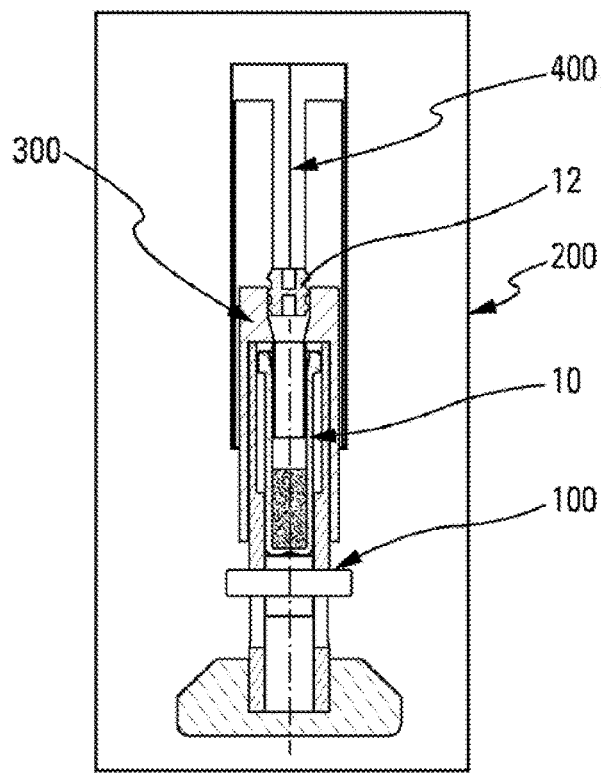
Figure 8:
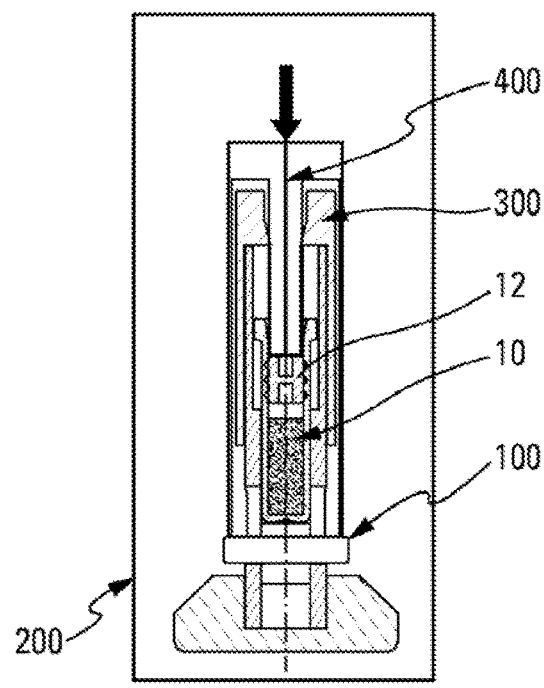

FIGS. 2 and 3 compare closing at atmospheric pressure (FIG. 2) and closing under a vacuum in accordance with the invention (FIG. 3). With the present invention, it can clearly be seen that the residual volume of air is reduced significantly, or even eliminated, and consequently that the residual volume of air present in said reservoir 10 between said fluid and said stopper 12 is substantially zero.

FIGS. 4 to 8 show the successive steps of an advantageous method of filling and closing.

The reservoir 10 is initially filled with the fluid, and then the filled reservoir 10 is arranged in a support device 100 that is adapted to hold said reservoir. The assembly is then placed in a vacuum chamber 200, and a vacuum is formed. A funnel 300 is then placed at the opening of the reservoir 10, and a stopper is pre-positioned in the funnel 300. A closure tool 400 is then positioned above the funnel 300, and moving said closure tool 400 axially moves said stopper 12 into the reservoir 10.

Preferably, the stopper is not pushed into contact with the fluid, and a space is deliberately left so as to ensure that the fluid does not pass beyond the sealing ridges of the stopper. When the closed reservoir 10 is removed from the vacuum chamber 200, the atmospheric pressure that is applied to the outside of the stopper 12 automatically moves said stopper 12 into contact with the fluid. If necessary, provision can be made to push said stopper 12 into contact with the fluid.

In another advantageous variant, the reservoir 10 could also be filled under a vacuum, e.g. in a filler and closure unit provided with a vacuum chamber. This would make it possible to prevent any contact between the fluid and the atmosphere, which may be desirable with certain sensitive pharmaceuticals.

The present invention provides several advantages, and in particular:
  it improves the reproducibility of the spray, reducing variations from one reservoir to another;
  it increases the distance between the tip 14 of the needle 13 and the stopper 12 before actuation; firstly this makes it possible to center the needle better relative to the stopper at the moment of piercing, consequently reducing the risk of hydraulic blocking; and secondly there is no longer any risk associated with the proximity between the needle and the stopper, such that the stopper can be positioned with positioning tolerances that are greater;
  it makes it possible to increase the volume of fluid during filling of the reservoir;
  it makes it possible to avoid, or at least, to greatly limit oxidation of the fluid on contact with air;
  it makes it possible to limit deformation of the stopper while it is being pierced.

Naturally, other variant embodiments may also be envisaged, without going beyond the ambit of the present invention, as defined by the accompanying claims.

The invention claimed is:

1. A fluid dispenser device comprising: a body; a reservoir containing one or two doses of a fluid, said reservoir including a stopper that closes said reservoir in leaktight manner before actuation; a dispenser head that is provided with a dispenser orifice; and dispenser means for dispensing at least a portion of said fluid through said dispenser orifice during actuation; said device includes a needle having a tip that is adapted to pierce said stopper during actuation, said reservoir being filled with said fluid and being closed with said stopper under a vacuum, so that a residual volume of air present in said reservoir between said fluid and said stopper is substantially zero.

2. A device according to claim 1, wherein said stopper is in contact with said fluid in the reservoir.

3. A device according to claim 1, wherein said needle is stationary relative to said dispenser orifice.

4. A method of filling and closing a fluid dispenser device comprising: a body; a reservoir containing one or two doses of a fluid, said reservoir including a stopper that closes said reservoir in leaktight manner before actuation; a dispenser head that is provided with a dispenser orifice; and dispenser means for dispensing at least a portion of said fluid through said dispenser orifice during actuation; said device including a needle having a tip that is adapted to pierce said stopper during actuation, said method comprises the following steps:

filling an empty reservoir in a filler unit;
arranging said filled reservoir in a closure unit that is provided with a vacuum chamber;
creating a vacuum in said vacuum chamber; and
closing said reservoir under the vacuum with said stopper.

5. A method according to claim 4, wherein said closure unit comprises: a support device; said vacuum chamber; a funnel; and a closure tool.

6. A method according to claim 4, wherein said step of filling said empty reservoir in said filler unit is also performed under a vacuum.

* * * * *